United States Patent
Perkins et al.

(10) Patent No.: US 8,028,581 B2
(45) Date of Patent: Oct. 4, 2011

(54) METHODS AND SYSTEMS FOR ULTRASONIC INSPECTION OF ROTATING SHAFTS

(75) Inventors: Blair C. Perkins, Richmond, KY (US); Gordon E. Smith, Westerville, OH (US)

(73) Assignee: Toyota Motor Engineering & Manufacturing North America, Inc., Erlanger, KY (US)

( * ) Notice: Subject to any disclaimer, the term of this patent is extended or adjusted under 35 U.S.C. 154(b) by 580 days.

(21) Appl. No.: 12/188,523

(22) Filed: Aug. 8, 2008

(65) Prior Publication Data
US 2010/0031751 A1 Feb. 11, 2010

(51) Int. Cl.
*G01N 29/11* (2006.01)
(52) U.S. Cl. ............... 73/622; 73/592; 73/600; 73/602
(58) Field of Classification Search .............. 73/622, 73/579, 593, 600, 623, 628, 660, 599, 602
See application file for complete search history.

(56) References Cited

U.S. PATENT DOCUMENTS

| | | | |
|---|---|---|---|
| 3,961,523 A | 6/1976 | Cornforth | |
| 4,422,333 A * | 12/1983 | Leon | 73/660 |
| 4,478,082 A * | 10/1984 | Sato et al. | 73/593 |
| 4,660,419 A | 4/1987 | Derkacs et al. | |
| 4,899,590 A | 2/1990 | Light et al. | |
| 5,078,954 A | 1/1992 | Smith et al. | |
| 5,160,876 A * | 11/1992 | Niinai et al. | 318/460 |
| 5,189,915 A | 3/1993 | Reinhart et al. | |
| 5,566,092 A * | 10/1996 | Wang et al. | 702/185 |
| 6,659,712 B2 * | 12/2003 | Brooks et al. | 415/1 |
| 6,668,655 B2 * | 12/2003 | Harrold et al. | 73/660 |
| 6,707,297 B2 * | 3/2004 | Nath et al. | 324/240 |
| 7,650,790 B2 * | 1/2010 | Wright | 73/622 |
| 7,654,143 B2 * | 2/2010 | Roney et al. | 73/620 |
| 7,735,370 B2 * | 6/2010 | Burat et al. | 73/660 |
| 7,805,997 B2 * | 10/2010 | Yu et al. | 73/622 |
| 7,841,237 B2 * | 11/2010 | Suzuki et al. | 73/623 |

* cited by examiner

*Primary Examiner* — J M Saint Surin
(74) *Attorney, Agent, or Firm* — Dinsmore & Shohl LLP

(57) ABSTRACT

A method of inspecting a rotatable shaft for the presence of defects may include continuously rotating a shaft under an applied load. As the shaft is rotated, an ultrasonic signal may be propagated along the length of the shaft. Attenuated or reflected ultrasonic signals may be collected from the shaft as the shaft is rotated. The presence of a defect in the shaft is determined by analyzing the collected ultrasonic signals.

19 Claims, 5 Drawing Sheets

METHODS AND SYSTEMS FOR ULTRASONIC INSPECTION OF ROTATING SHAFTS

TECHNICAL FIELD

The present invention generally relates to methods and systems for inspecting load-bearing shafts and, more specifically, to ultrasonic methods and systems for inspecting load-bearing, rotating shafts.

BACKGROUND

Rotating components such as axles, shafts and the like may be subject to fatigue cracking particularly when the rotating component is subject to unbalanced loading conditions. Left undiagnosed, such cracking may ultimately lead to a catastrophic failure of the rotating component. When the rotating component is a conveyor shaft or similar component employed in a manufacturing operation, failure of the rotating component may shut down the manufacturing operation thereby resulting in significant economic losses.

To prevent failure, the rotating component may be regularly and frequently inspected for fatigue cracks or other damage which may lead to cracking as a matter of routine preventative maintenance. Current methods for inspecting a rotating component for cracks may involve the use of eddy-current inspection devices, meandering-wandering magnetometer inspection devices, x-ray diffraction, mag-particle testing, dye-penetrant inspection, and the like. While such techniques and devices are well suited for identifying the smallest of cracks, none of the techniques and/or devices are particularly well suited for the in situ inspection of the rotating component while the component is actually rotating. More specifically, the above referenced techniques generally require that the rotating component be removed from the apparatus in which it is installed in order for the inspection to be performed which, in turn, may cause costly process down time. In certain situations these preventative maintenance measures may be nearly as costly as the failure of the rotating component.

Accordingly, a need exists for alternative methods and systems for inspecting rotating shafts for cracks.

SUMMARY

In one embodiment, a method of inspecting a rotatable shaft for the presence of defects may include propagating an ultrasonic signal along a length of the shaft as the shafted is continuously rotated about an axis of rotation under an applied load. Ultrasonic signals are collected from the shaft as the shaft is rotating under the applied load. The presence of a defect is determined based on the collected ultrasonic signals.

In another embodiment, a method for inspecting a solid rotating shaft for defects in situ may include propagating an ultrasonic signal along a length of the shaft as the shaft is continuously rotated under an applied load such that, if a defect is present in the shaft, the defect opens and closes as the shaft is rotated. Reflected ultrasonic signals are collected from the shaft and the presence of a defect in the shaft is determined based on a change in amplitude of the reflected ultrasonic signals as the shaft is rotated under the applied load.

In yet another embodiment, a system for inspecting a shaft for defects may include at least one shaft support, a tensioner, a rotational mechanism and an ultrasonic testing apparatus. The at least one shaft support may be operable to receive and support the shaft as the shaft is rotated. The tensioner may be operable to apply a load to the shaft positioned in the at least one shaft support thereby causing the shaft to deflect. The at least one rotational mechanism may be operable to impart continuous rotational motion to the shaft when the shaft is positioned in the at least one shaft support. The ultrasonic testing apparatus may comprise an ultrasonic transducer operatively coupled to a control unit. The ultrasonic transducer may be attachable to an end of a shaft positioned in at least one shaft support. The ultrasonic transducer may also be operable to propagate ultrasonic signals along a length of the shaft and receive reflected ultrasonic signals. The control unit may be operable to control a frequency and intensity of the ultrasonic signals propagated by the ultrasonic transducer and store and display the reflected ultrasonic signals received by the ultrasonic transducer.

BRIEF DESCRIPTION OF THE DRAWINGS

The embodiments set forth in the drawings are illustrative and exemplary in nature and not intended to limit the inventions defined by the claims. The following detailed description of the illustrative embodiments can be understood when read in conjunction with the following drawings, where like structure is indicated with like reference numerals and in which:

DETAILED DESCRIPTION OF THE ILLUSTRATIVE EMBODIMENTS

Figure 1:
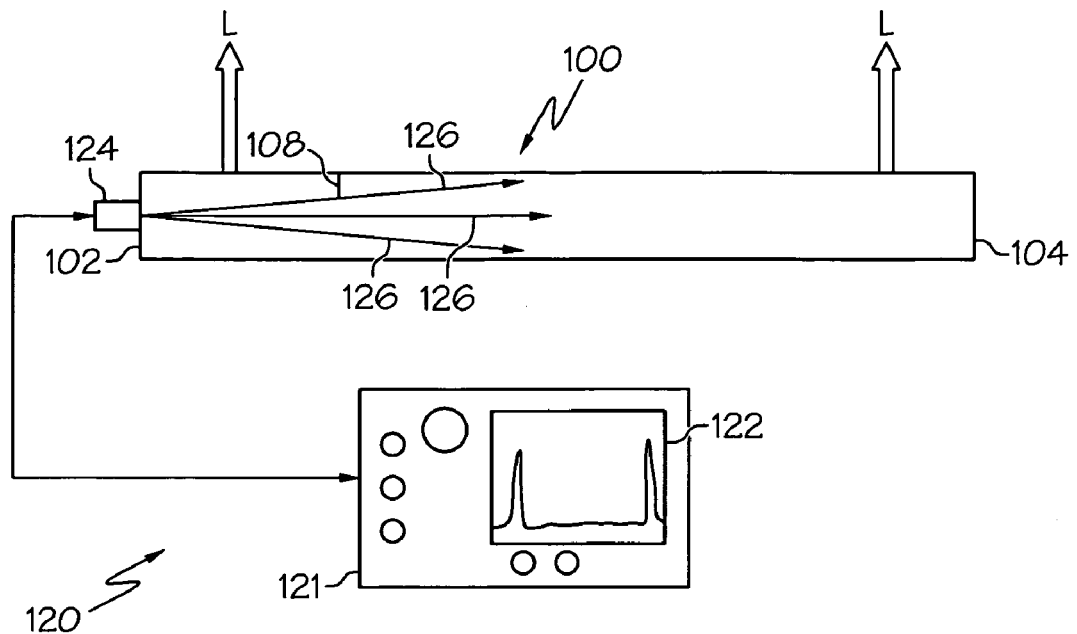
FIG. 1 depicts an ultrasonic testing apparatus attached to a rotating shaft according to one embodiment described herein.

FIG. 1 generally depicts an ultrasonic testing apparatus attached to a rotatable shaft for performing the method of inspecting rotating shafts described herein. The method generally comprises affixing an ultrasonic transducer to the end of a shaft such that a high-frequency ultrasonic signal may be propagated along the length of the shaft while the shaft is continuously rotated under an applied load. Ultrasonic signals reflected by defects in the rotating shaft are received by the transducer and passed to a control unit where the reflected ultrasonic signals may be displayed and analyzed. The systems and methods of performing ultrasonic inspection of rotating shafts will be discussed in more detail herein.

Referring now to FIG. 1, an ultrasonic testing apparatus 120 is depicted connected to a rotatable shaft 100. The ultrasonic testing apparatus 120 generally comprises an ultrasonic transducer 124 operatively connected to a control unit 121. The ultrasonic transducer 124 may be operable to both propagate and receive a high frequency ultrasonic signal such as when the ultrasonic testing apparatus 120 is configured for a pulse-echo mode of operation. In one embodiment, the ultrasonic transducer 124 may be operatively connected to the control unit 121 with a cable, wire or other, similar connector. In another embodiment, the ultrasonic transducer 124 may be wirelessly connected to the control unit 121.

Still referring to FIG. 1, the control unit 121 may be operable to control the frequency and intensity of the ultrasonic signal (e.g., an ultrasonic pulse) propagated by the ultrasonic transducer 124. The control unit 121 may also be operable to record reflected ultrasonic signals (e.g., ultrasonic echoes) received by the ultrasonic transducer 124. The control unit 121 may comprise a display 122 for displaying an electronic signal indicative of a reflected ultrasonic signal received by the ultrasonic transducer 124. Alternatively, the control unit 121 may be operatively coupled to an oscilloscope or monitor for displaying an electronic signal indicative of a reflected ultrasonic signal received by the ultrasonic transducer 124. The control unit 121 may also be operable to record signals received from the ultrasonic transducer 124 such as when the control unit 121 comprises a hard drive, solid state hard drive or a similar electronic storage device.

In one embodiment, the ultrasonic transducer may produce an ultrasonic signal having a frequency from about 0.1 MHz to about 50 MHz. In another embodiment, the ultrasonic transducer may comprise a one inch diameter ultrasonic transducer having a center frequency of about 2.25 MHz and an output frequency range from about 1 MHz to about 5 MHz. In another embodiment, the ultrasonic transducer may comprises a one inch diameter ultrasonic transducer having a center frequency of about 1 MHz and an output frequency range from about 0.5 MHz to about 2.5 MHz. The control unit may comprise a Stavely S30 reflectoscope or similar ultrasonic control unit. In one embodiment, the ultrasonic transducer may be operatively coupled to the control unit with a UG174 cable. However, other combinations of ultrasonic transducers, cables and control units may be used as will be apparent to one skilled in the art.

The rotatable shaft 100 depicted in FIGS. 1-4 may be a take-up shaft utilized in an automobile conveyor system. However, it should be understood that the shaft 100 may be any rotating shaft including, without limitation, steam turbine shafts, gas turbine shafts, automobile and rail car axles, power transmission shafts and the like. The shaft 100 may be solid and generally extend in an axial direction between a first end 102 and a second end 104. The shaft may be rotatable about an axis of rotation 106 which generally extends between the first end 102 and the second end 104. The ultrasonic transducer 124 may be affixed to either the first end 102 or second end 104 of the shaft 100 such that the face of the ultrasonic transducer is substantially perpendicular to the axis of rotation 106 of the shaft 100. The ultrasonic transducer 124 may be attached to the shaft 100 using a mechanical clamp, an adhesive, a suction cup or similar attachment device. In one embodiment, grease, oil, gel or a similar coupling material may be disposed between the ultrasonic transducer 124 and the end of the shaft to eliminate air between the ultrasonic transducer 124 and the shaft 100 and thereby improve the coupling of the ultrasonic signal propagated by the ultrasonic transducer 124 into the shaft 100.

Figure 2:
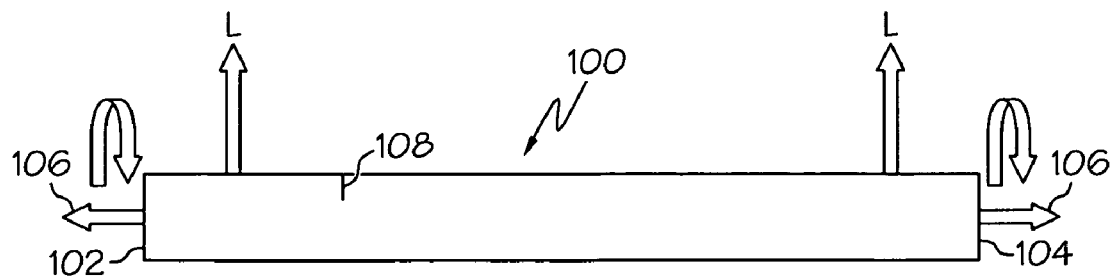
FIG. 2 depicts a rotating shaft with a defect, specifically a crack, under an applied load oriented such that the crack is closed.
Figure 3:
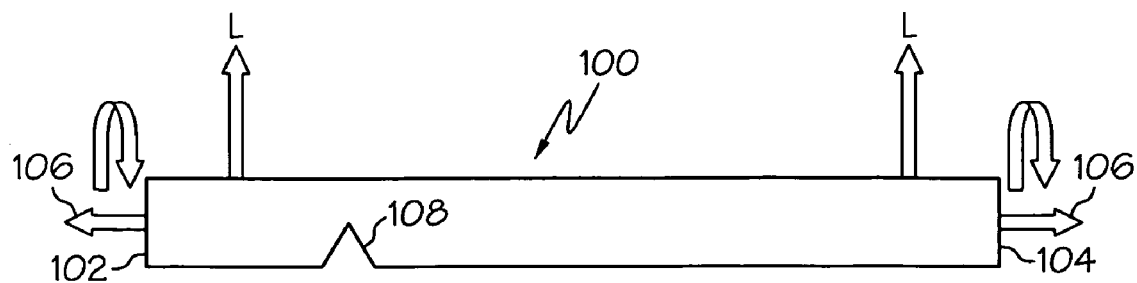
FIG. 3 depicts the rotating shaft of FIG. 2 oriented such that the crack is open.

Referring now to FIGS. 2 and 3, the shaft 100 may be subject to an applied load L as generally indicated in FIGS. 2 and 3. The applied load L may be generally applied to the shaft 100 in a substantially radial direction. The shaft 100 may also contain a defect, such as a crack 108. When the crack 108 is oriented such that the crack 108 is under compression due to the applied load L, as shown in FIG. 2, the crack 108 is pressed together, essentially pressing or squeezing both halves of the crack face together such that the crack 108 is closed (e.g., there is no discontinuity in the shaft).

However, when the shaft 100 is oriented such that the crack 108 is under tension due to the applied load L, as shown in FIG. 3, the crack 108 is pulled open forming a discontinuity in the shaft 100. Accordingly, as the shaft 100 rotates about the axis 106 under the applied load L, the crack 108 opens and closes in synchronization with the rotation of the shaft 100. As such, the opening and closing of the crack 108 is substantially cyclical for a rotating shaft.

Figure 4:
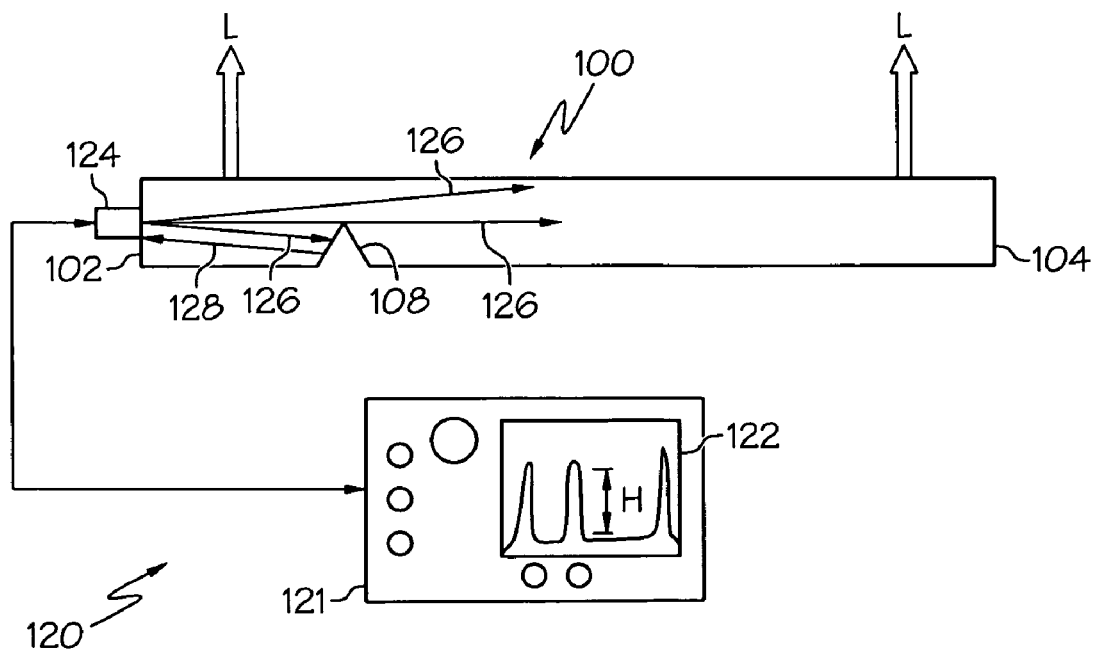
FIG. 4 depicts the ultrasonic testing apparatus of FIG. 1 wherein the shaft is oriented such that a crack in the shaft is open.

Referring again to FIG. 1, when the shaft 100 is oriented such that the crack 108 is closed, an ultrasonic signal 126 introduced into the shaft 100 by the ultrasonic testing apparatus 120 propagates through the shaft between the first end 102 and second end 104. The ultrasonic signal introduced into the shaft 100 may have a frequency from about 0.1 MHz to about 50 MHz. The propagated ultrasonic signal 126 may pass through the closed crack 108 without any substantial reflection of the ultrasonic signal as the shaft 100 is substantially continuous when the crack is closed. However, when the propagated ultrasonic signal 126 encounters an open crack 108, such as when the shaft 100 is oriented such that the crack 108 is open as depicted in FIG. 4, the propagated ultrasonic signal 126 is reflected towards the ultrasonic transducer 124 due to the discontinuity in the material of the shaft. The reflected ultrasonic signal 128 is received by the ultrasonic transducer 124 which converts the reflected ultrasonic signal 128 to an electronic signal. The electronic signal may be passed to the control unit 121 of the ultrasonic testing apparatus 120 which, in turn, displays the electronic signal on the display 122. The intensity of the reflected ultrasonic signal 128 received by the ultrasonic transducer 124 may generally correspond to the height or amplitude of the electronic signal displayed on the display 122, which, in turn, may be proportional to the distance which the crack 108 is open. Accordingly, by positioning the ultrasonic transducer 124 on an end of the shaft 100 and propagating an ultrasonic signal along the shaft 100 while the shaft 100 is rotating about the axis of rotation 106 under an applied load L, the shaft 100 may be inspected for the presence of cracks by monitoring and collecting the reflected ultrasonic signals 128. An electronic signal displayed on the display 122 and having a amplitude which oscillates in synchronization with the rotation of the shaft 100 may be generally indicative of the presence of a crack opening and closing as the shaft rotates under an applied load.

While the embodiments shown in FIGS. 1 and 4 generally show an ultrasonic testing apparatus 120 configured for pulse-echo operation, it should be understood that the ultrasonic testing apparatus may also be configured for an attenuation mode of operation. For example, in another embodiment (not shown) the ultrasonic testing apparatus may comprise an ultrasonic transducer and a separate receiver, both of which are operatively connected to the control unit of the ultrasonic testing apparatus. In this embodiment, the ultrasonic transducer and receiver may be positioned on opposite ends of the shaft such that an ultrasonic signal introduced into the shaft by the ultrasonic transducer is received by the receiver located at the opposite end of the shaft. The receiver converts the received ultrasonic signals to electronic signals and passes the electronic signals to the control unit where the electronic signals are stored and displayed. As discussed hereinabove, the amplitude of the electronic signal displayed by the control unit may be generally indicative of the intensity of the received ultrasonic signals. In this mode of operation the attenuation of the propagated ultrasonic signal over the length of the shaft may be indicative of features and/or defects such as cracks contained in the shaft.

Figure 5C:
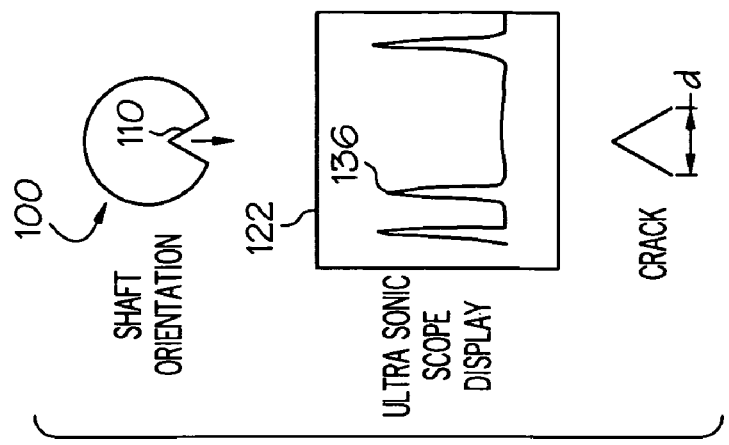
FIG. 5 depicts reflected ultrasonic signals displayed on the display of a control unit for various rotational orientations of the rotating shaft and the corresponding state (e.g., open or closed) of the crack.
Figure 5B:
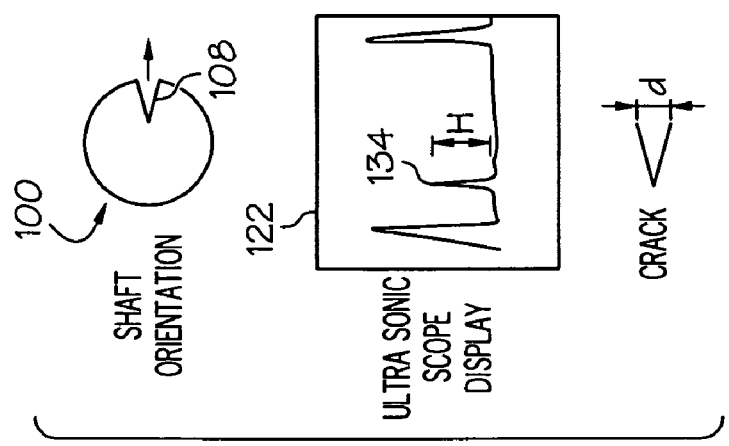
Figure 5A:
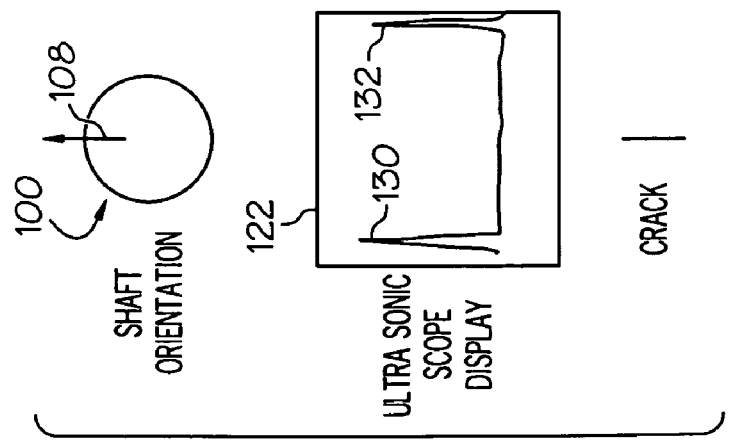

Referring now to FIGS. 5A-5E, the signal received from the ultrasonic transducer 124 is shown for various rotational orientations of the shaft 100 as the shaft is continuously rotated. As shown in FIG. 5A, when the shaft 100 is oriented such that the crack 100 is closed due to the applied load L, the reflected ultrasonic signals received by the ultrasonic transducer generally comprise a first peak 130 and a second peak 132. The first peak 130 may be a reflection of the propagated ultrasonic signal from the interface of the ultrasonic transducer 124 with the end of the shaft 100. The second peak 134 may be a reflection of the propagated ultrasonic signal 126 from a feature (not shown), such as a keyway, groove or the like, contained in the shaft 100. Where the shaft 100 is a take-up shaft used in a conveyor system, as shown in FIGS. 1-4, the second peak 134 is a reflected ultrasonic signal from a keyway. Because the crack 108 is closed for the shaft orientation shown in FIG. 5a, the propagated ultrasonic signal is not reflected by the crack 108 and, as such, the display does not indicate a peak corresponding to the presence of a crack. Accordingly, the signal shown on the display 122 may be indicative of a baseline signature showing reflected ultrasonic signals for features present in the shaft irrespective of the orientation of the shaft.

In one embodiment, a baseline signature as shown in FIG. 5A may be obtained for a particular shaft when the shaft 100 is first installed and presumably crack and/or defect free. As discussed hereinabove, the baseline signature for the shaft will generally show reflections from features inherent in the shaft. Thereafter, signatures obtained during subsequent testing may be compared to the baseline signature to determine if cracks may have formed in the shaft during operation.

In FIG. 5B the shaft 100 is rotated 90 degrees from the initial orientation shown in FIG. 5A. In this orientation, the crack 108 is opened due to the load L applied to the shaft 100. The propagated ultrasonic signal is reflected by the open crack 108 and the reflected ultrasonic signal is received by the ultrasonic transducer where it is converted to an electronic signal and displayed on the display 122 as a crack reflection peak 134. The height H or amplitude of the crack reflection peak 134 is generally indicative of the intensity of the reflected ultrasonic signal received by the ultrasonic transducer which is, in turn, generally indicative of the distance which the crack is open. Accordingly, in one embodiment, the height H of the crack reflection peak 134 may be calibrated such that the distance which a crack is opened may be determined from the display.

Further, in another embodiment, the position of the crack 108 relative to the end of the shaft 100 may also be determined from the position of the crack reflection peak 134 relative to the first peak 130 and the second peak 132. More specifically, as discussed hereinabove, the first peak 130 and the second peak 132 may be indicative of features contained on the shaft (specifically the end of the shaft and another feature). The position of these features may be directly measured on the actual shaft 100. For example, when the shaft contains a keyway as discussed herein, the position of the keyway from an end of the shaft may be directly measured. Thereafter, the direct measurements of shaft features may be used in conjunction with the distance between the first peak 130 and the second peak 132 as measured on the display 122 to calibrate the display 122 such that the position of the crack reflection peak 134 on the display 122 may be used to determine the actual position of a crack 108 on the shaft 100.

In FIG. 5C the shaft 100 is rotated 180 degrees from the initial orientation shown in FIG. 5A. In this orientation, the crack 108 is opened further due to the load applied to the shaft 100. Accordingly, the crack reflection peak 134 in FIG. 5C has a height H greater than the crack reflection peak shown in FIG. 5B. In the orientation shown in FIG. 5C, the shaft 100 may be positioned such that the load L applied to the shaft 100 causes the crack 108 to open the maximum distance.

Figure 5E:
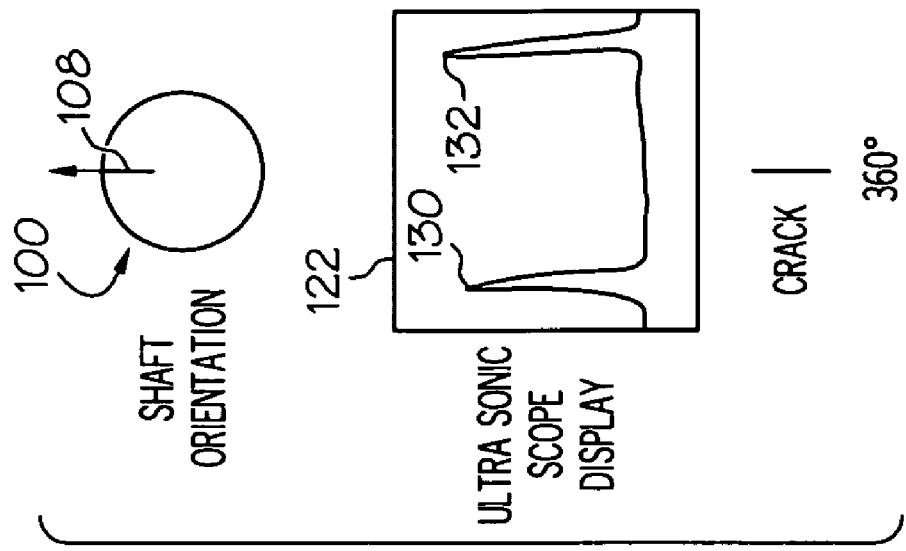
Figure 5D:
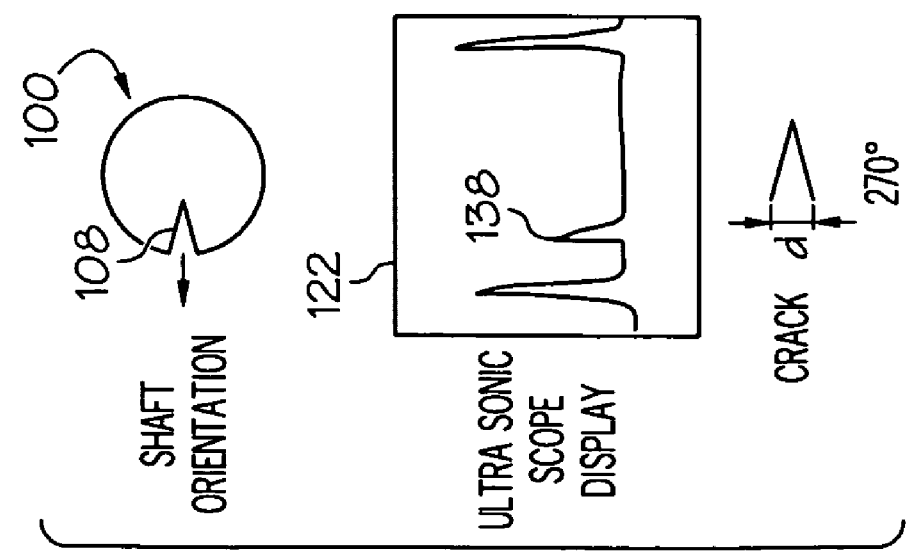

In FIG. 5D the shaft 100 is rotated 270 degrees from the initial orientation shown in FIG. 5A. When the shaft is in this orientation the crack 108 is closing and the distance which the crack is open is less than the crack opening shown in FIG. 5C. Accordingly, the crack reflection peak 134 shown in FIG. 5D has a height H which is less than the crack reflection peak 134 shown in FIG. 5C.

Finally, in FIG. 5E, the shaft 100 has been rotated a full 360 degrees and is returned to the starting position. In this orientation the crack 108 is under compression due to the applied load on the shaft 100. As such, the crack 108 is completely closed and the propagated ultrasonic signals pass through the crack 108 without being reflected. Accordingly, no cracks reflection peak is displayed on the display 122 for this orientation.

As shown in FIGS. 5A-5E, the height H or amplitude of the crack reflection peak 134 is synchronized with the opening and closing of the crack 108 which is, in turn, synchronized with the rotation of the shaft 100 while under an applied load. Accordingly, by collecting reflected ultrasonic signals while the shaft is continuously rotated under an applied load and identifying which of the reflected ultrasonic signals are synchronized with the continuous rotation of the shaft 100, the shaft 100 may be inspected for the presence of cracks. In one embodiment, the collected reflected ultrasonic signals may be compared to a baseline signature for a crack-free shaft. Peaks appearing in the collected reflected ultrasonic signals and not the baseline signature will generally indicate the presence of a crack. In another embodiment, the collected reflected ultrasonic signals are analyzed to determine if the amplitude of any of the reflection peaks oscillate or fluctuate with rotation of the shaft. A peak that generally oscillates in synchronization with the rotation of the shaft (e.g., the height or amplitude of the peak increases and decreases in a cyclical manner with the rotation of the shaft) may generally indicate the presence of a crack in the shaft. Upon identifying the presence of a crack, the position of the reflected ultrasonic signals indicating the presence of a crack may be used to determine the position of the crack(s) in the shaft as well as the distance or amount the crack opens as the shaft is rotated.

The method described hereinabove may be used to inspect a shaft for cracks in situ (e.g., without removing the shaft from the equipment or apparatus in which the shaft is installed) while equipment is in operation and the shaft is continuously rotated. Accordingly, the method may be used in conjunction with routine maintenance and inspection of the equipment without requiring time consuming and expensive disassembly of the equipment to assess the condition of the shaft. However, it should be understood that the method described herein may also be used to inspect shafts that have been removed from the equipment or apparatus in which they are installed.

Figure 6:
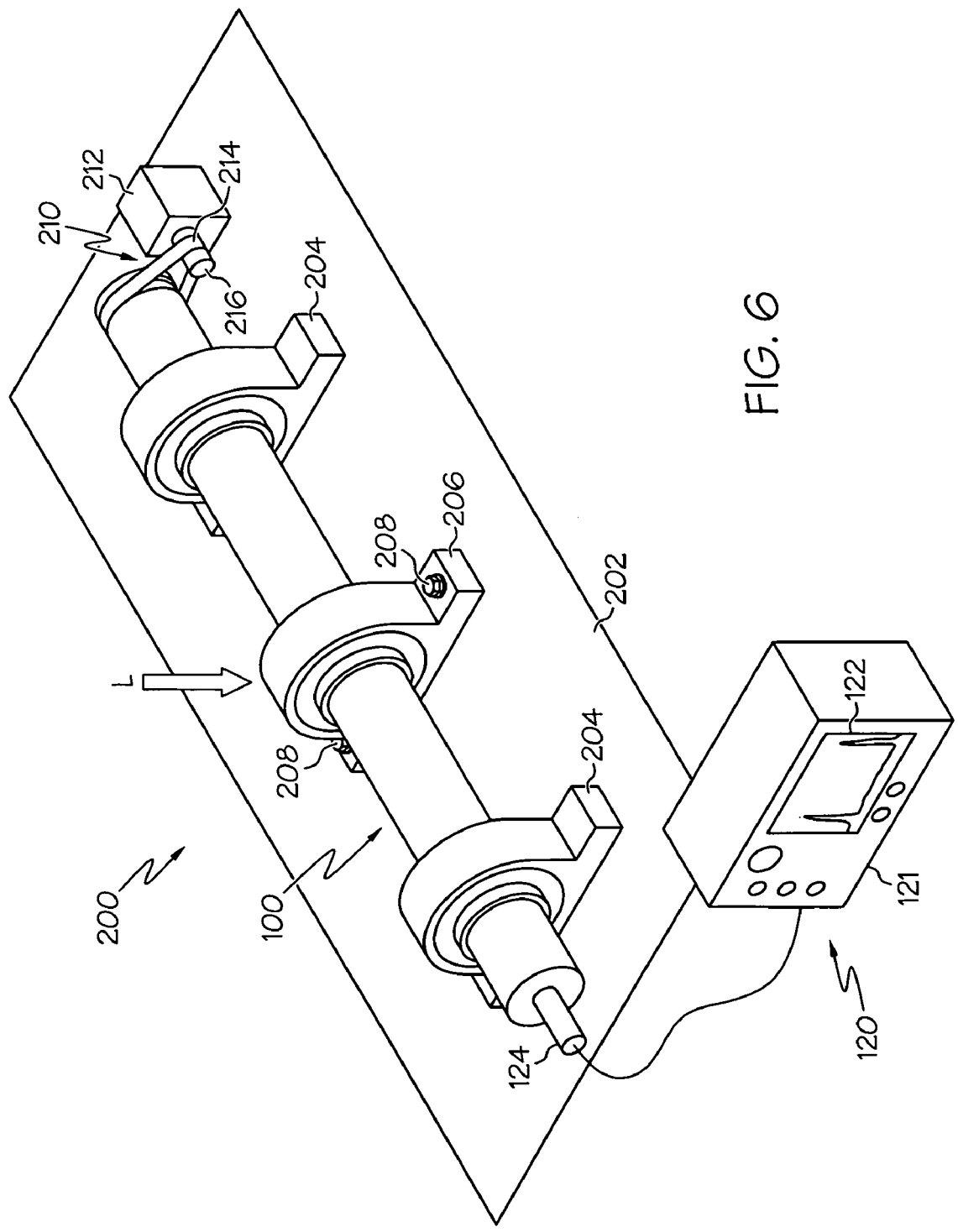
FIG. 6 depicts a system for inspecting rotating shafts for cracks according to one embodiment shown and described herein.

Referring now to FIG. 6, a system 200 for inspecting shafts for cracks is shown. The system 200 generally comprises an ultrasonic testing apparatus 120 comprising an ultrasonic transducer 124 and control unit 121, a shaft support 204, a tensioner 206, and a rotational mechanism 210. The system 200 may be secured to a platform 202 such as a table, workbench or the like. The shaft support 204 may comprise a bearing or rollers that support the shaft 100 as the shaft is rotated. In the embodiment shown in FIG. 6 the shaft supports 204 comprise bearings through which the shaft 100 is inserted. It should be understood that, while the embodiment of the system 200 shown in FIG. 6 is depicted as having two shaft supports 204, the number of shaft supports used in the system may vary depending on the size of the shaft being inspected and the characteristics of the load applied to the shaft. Accordingly, the system 200 may comprise one shaft support or a plurality of shaft supports as shown in FIG. 6.

The tensioner 206 is operable to apply a load L to the shaft 100 while also allowing the shaft to freely rotate. In the embodiment of the system 200 shown in FIG. 6, the tensioner 206 comprises a bearing that is disposed between the two shaft supports 204. The shaft 100 passes through the tensioner 206 such that the shaft is free to rotate. The load L applied to the shaft 100 by the tensioner 206 may be adjusted by turning bolts 208 which fasten the tensioner 206 to the platform 202. By tightening the bolts 208, the tensioner 206 is drawn towards the platform 202 thereby deflecting the shaft 100 towards the platform and increasing the load L on the shaft. Loosening the bolts 208 decreases the load L on the shaft 100 as well as the amount of deflection in the shaft 100.

The rotational mechanism 210 is operable to impart continuous rotational motion to the shaft 100. In the embodiment shown in FIG. 6, the rotational mechanism 210 comprises a motor 212 with a rotating armature 216. The armature 216 is coupled to the shaft by a belt 214 such that the rotation of the armature is imparted to the shaft 100. In another embodiment (not shown), the rotational mechanism may comprise a hand crank or lever attached to the end of the shaft such that the shaft may be manually rotated. Accordingly, it should be understood that other rotational mechanisms may be used to impart rotational motion to the shaft 100.

The ultrasonic testing apparatus 120 may generally comprise an ultrasonic transducer and a control unit as described above with respect to FIG. 1. The ultrasonic transducer may be attached to the shaft 100 as described above with the ultrasonic transducer 124 affixed to the end of the shaft using a mechanical clamp, an adhesive, a suction cup or similar attachment device. In one embodiment, grease, oil, gel or a similar coupling material is disposed between the ultrasonic transducer 124 and the end of the shaft to eliminate air between the ultrasonic transducer 124 and the shaft 100 and thereby improve the coupling of the ultrasonic signal transmitted by the ultrasonic transducer 124 into the shaft 100.

In operation, the shaft 100 may be inserted into the system 200 such that the shaft is inserted through the shaft supports 204 and the tensioner 206. The shaft 100 may be coupled to the rotational mechanism 210 by positioning the belt 214 around the shaft 100. The desired load L may then be applied to the shaft 100 by tightening the bolts 208 on the tensioner 206. The ultrasonic transducer 124 may be attached to the end of the shaft 100. Thereafter, the shaft may be continuously rotated by the rotational mechanism 210 while ultrasonic signals are propagated along the length of the shaft via the ultrasonic transducer 124 as described above. Reflected ultrasonic signals may be collected by the transducer and analyzed as described herein to determine if cracks are present in the shaft 100.

The ultrasonic method and system for inspecting rotating shafts shown and described herein may be used to inspect a rotating shaft for cracks and/or other defects as a matter of routine maintenance. When a crack is identified the position and size of the crack may be assessed and, based on this assessment, a determination may be made as to whether the shaft should be replaced immediately or whether the shaft may remain in service and replacement scheduled for a future date. When the ultrasonic method for inspecting rotating shafts is used in this manner equipment and/or process downtime may be mitigated.

It should now be understood that the ultrasonic method for inspecting shafts shown and described herein may be used to determine the presence of cracks in a shaft while the shaft is rotated under an applied load. The ultrasonic method may also be used to determine the position of cracks in the shaft and the maximum distance which the crack opens due to the applied load. Because the method utilizes the rotation of the shaft to facilitate opening and closing the crack, the method may be performed in situ, without removing the shaft from the equipment or machinery in which the shaft is installed thereby eliminating or reducing equipment downtime and reducing the overall inspection and maintenance costs associated with the equipment or machinery. However, it will also be understood that the ultrasonic inspection method shown and described herein may also be used in conjunction with the system shown and described herein to facilitate bench inspection of shafts removed from the equipment and machinery in which they are installed.

It should also be understood that the ultrasonic inspection method described herein may be used on rotating shafts including, without limitation, conveyor shafts, turbine shafts, automotive axels, railcar axels and the like.

While particular embodiments and aspects of the present invention have been illustrated and described herein, various other changes and modifications can be made without departing from the spirit and scope of the invention. Moreover, although various inventive aspects have been described herein, such aspects need not be utilized in combination. It is therefore intended that the appended claims cover all such changes and modifications that are within the scope of this invention.

What is claimed is:

1. A method of inspecting a rotatable shaft for the presence of defects, the method comprising:
propagating an ultrasonic signal along a length of the shaft with an ultrasonic transducer as the shaft is continuously rotated about an axis of rotation under an applied load;
collecting ultrasonic signals from the shaft as the shaft is rotating; and
determining if a defect is present in the shaft based on the collected ultrasonic signals, wherein the collected ultrasonic signal is indicative of a defect in the shaft if an amplitude of the collected ultrasonic signal increases and decreases in synchronization with the rotation of the shaft.

2. The method of claim 1 wherein determining if a defect is present in the shaft comprises comparing the collected ultrasonic signals to a baseline signature for a shaft without defects.

3. The method of claim 1 further comprising determining a position of the defect in the shaft when the collected ultrasonic signals are indicative of a defect in the shaft.

4. The method of claim 3 wherein the position of the defect in the shaft is determined based on collected ultrasonic signals corresponding to measurable features on the shaft.

5. The method of claim 1 wherein the ultrasonic transducer is attached to an end of the shaft and the ultrasonic transducer is operatively connected to a control unit operable to control a frequency and intensity of the ultrasonic signal propagated along the shaft.

6. The method of claim 5 wherein the collected ultrasonic signals are reflected ultrasonic signals and the ultrasonic transducer is operable to collect reflected ultrasonic signals, convert the reflected ultrasonic signals to electronic signals indicative of the reflected ultrasonic signals, and pass the electronic signals to the control unit; and the control unit is operable to receive electronic signals from the ultrasonic transducer, store the electronic signals from the ultrasonic transducer in a memory and display the electronic signals on a display.

7. The method of claim 5 wherein the collected ultrasonic signals are attenuated ultrasonic signals and the attenuated ultrasonic signals are collected and converted to electronic signals by a receiver attached to an end of the shaft opposite the ultrasonic transducer and wherein the receiver is operatively connected to the control unit; and the control unit is operable to receive electronic signals from the receiver, store the electronic signals from the ultrasonic transducer in a memory and display the electronic signals on a display.

8. The method of claim 1 wherein the shaft comprises a take-up shaft for an automobile conveyor system.

9. The method of claim 1 wherein the ultrasonic signal propagated along the length of the shaft has a frequency from about 0.1 MHz to about 50 MHz.

10. The method of claim 1 wherein the shaft is inspected in situ.

11. A method for inspecting a solid rotating shaft for defects, the method comprising:

propagating an ultrasonic signal along a length of the shaft as the shaft is continuously rotated under an applied load such that, if a defect is present in the shaft, the defect opens and closes as the shaft is rotated;

collecting reflected ultrasonic signals from the shaft; and determining if a defect is present in the shaft based on a change in amplitude of the reflected ultrasonic signals as the shaft is rotated under the applied load.

12. The method of claim 11 wherein when a defect is present, the amplitude of the reflected ultrasonic signal corresponding to the defect increases and decreases in synchronization with the rotation of the shaft.

13. The method of claim 11 wherein determining if a defect is present comprises comparing the reflected ultrasonic signals to a baseline signature for an undamaged shaft.

14. The method of claim 11 further comprising determining a position of the defect in the shaft based on the reflected ultrasonic signals.

15. The method of claim 14 wherein the position of the defect in the shaft is determined based on reflected ultrasonic signals corresponding to measurable features on the shaft.

16. The method of claim 11 wherein:

the ultrasonic signal is propagated along the length of the shaft by an ultrasonic transducer attached to an end of the shaft;

the ultrasonic transducer is operatively connected to a control unit for controlling a frequency and intensity of the ultrasonic signal propagated along the length shaft;

the ultrasonic transducer is operable to collect reflected ultrasonic signals, convert the reflected ultrasonic signals to electronic signals indicative of the reflected ultrasonic signals and pass the electronic signals to the control unit; and the control unit is operable to receive the electronic signals from the ultrasonic transducer, store the electronic signals from the ultrasonic transducer in a memory and display the electronic signals on a display.

17. The method of claim 16 wherein the display is calibrated such that a position of a defect in the shaft may be determined based on the displayed electronic signals.

18. The method of claim 11 wherein the ultrasonic signal propagated along the length of the shaft has a frequency from about 0.1 MHz to about 50 MHz.

19. A system for inspecting a shaft for defects, the system comprising at least one shaft support, a tensioner, a rotational mechanism and an ultrasonic testing apparatus wherein:

the at least one shaft support is operable to receive the shaft and support the shaft as the shaft is rotated;

the tensioner is operable to apply a load to the shaft positioned in the at least one shaft support thereby causing the shaft to deflect;

the at least one rotational mechanism is operable to impart continuous rotational motion to the shaft when the shaft is positioned in the at least one shaft support; and the ultrasonic testing apparatus comprises an ultrasonic transducer operatively coupled to a control unit wherein:

the ultrasonic transducer is attachable to an end of the shaft positioned in the at least one shaft support, the ultrasonic transducer being operable to propagate ultrasonic signals along a length of the shaft and receive reflected ultrasonic signals; and the control unit is operable to control a frequency and intensity of the ultrasonic signals propagated by the ultrasonic transducer and store and display reflected ultrasonic signals received by the ultrasonic transducer.

\* \* \* \* \*